(12) United States Patent
Amerio et al.

(10) Patent No.: US 10,478,288 B2
(45) Date of Patent: Nov. 19, 2019

(54) TRILEAFLET MECHANICAL PROSTHETIC HEART VALVE

(71) Applicant: Clover Life Sciences Inc., Buenos Aires (AR)

(72) Inventors: Osvaldo N. Amerio, Posadas (AR); Carlos Enrique Schvezov, Posadas (AR)

(73) Assignee: Clover Life Sciences Inc., Buenos Aires (AR)

( * ) Notice: Subject to any disclaimer, the term of this patent is extended or adjusted under 35 U.S.C. 154(b) by 0 days.

(21) Appl. No.: 14/870,049

(22) Filed: Sep. 30, 2015

(65) Prior Publication Data

US 2017/0086969 A1  Mar. 30, 2017

(51) Int. Cl.
*A61F 2/24* (2006.01)

(52) U.S. Cl.
CPC .............. *A61F 2/2403* (2013.01); *A61F 2/24* (2013.01); *A61F 2230/0071* (2013.01)

(58) Field of Classification Search
CPC ................................. A61F 2/2403; A61F 2/24
See application file for complete search history.

(56) References Cited

U.S. PATENT DOCUMENTS

| | | | |
|---|---|---|---|
| 4,078,268 A * | 3/1978 | Possis | A61F 2/2403 137/512.1 |
| 4,820,299 A | 4/1989 | Philippe et al. | |
| 4,878,909 A | 11/1989 | Parravicini | |
| 5,236,448 A | 8/1993 | Angelini et al. | |
| 5,562,730 A | 10/1996 | Davidson | |
| 5,628,792 A | 5/1997 | Lentell | |
| 6,059,826 A * | 5/2000 | Bokros | A61F 2/2403 623/2.11 |
| 7,371,258 B2 | 5/2008 | Woo et al. | |

(Continued)

FOREIGN PATENT DOCUMENTS

| | | |
|---|---|---|
| AR | 020714 A1 | 5/2002 |
| AR | 042291 | 6/2005 |
| CN | 204219096 | 3/2015 |

OTHER PUBLICATIONS

PCT International Search Report and Written Opinion for PCT/US2016/053992, dated Dec. 15, 2016, 11 Pages.

(Continued)

*Primary Examiner* — Dinah Baria
(74) *Attorney, Agent, or Firm* — Fenwick & West LLP

(57) ABSTRACT

A mechanical prosthetic heart valve having a ring, multiple hinges, and multiple leaflets. The hinges are attached to the ring and are evenly spaced from one another along the inner circumference of the ring. Each leaflet is rotably attached to a hinge by an opening located in the center of the lower portion of the leaflets. The ring can include multiple protrusions located along the inner circumference of the ring. The protrusions of the ring limit the opening angle of the leaflets. By limiting the opening angle of the leaflets, wear and tear of the hinges and leaflets, as well as the probability of malfunction of the mechanical prosthetic heart valve are reduced. In addition, limiting the opening angle of the leaflets may increase the opening and closing speed of the leaflets, thus improving performance of the mechanical prosthetic heart valve when the patient is experiencing an elevated cardiac frequency.

22 Claims, 9 Drawing Sheets

(56) References Cited

U.S. PATENT DOCUMENTS

| | | | |
|---|---|---|---|
| 7,658,727 B1 | 2/2010 | Fernandes et al. | |
| 2008/0086202 A1* | 4/2008 | Lapeyre | A61F 2/2403 623/2.33 |
| 2010/0023121 A1* | 1/2010 | Evdokimov | A61F 2/2403 623/2.36 |
| 2012/0059455 A1* | 3/2012 | Weber | A61L 31/022 623/1.42 |

OTHER PUBLICATIONS

Rosenberger, M., et al., "Disetio optimizado de una prótesis mecánica de válvula cardiaca de tres valvas," 3as Jornadas de Investigación Científico Tecnológicas 2005 de la UNaM, Mecanica Computacional vol. XXIV, Nov. 2005, pp. 1943-1957, Can be retrieved at <URL:http://www.cimec.org.ar/ojs/index.php/mc/article/viewFile/146/133>. With English Abstract.

Rosenberger, M., et al., "Modelizacion, diseño y construcción de un prototipo de prótesis de válvula cardiac," 14 Congreso Cientifico Internacional, Revista CENIC Ciencias Biológicas, vol. 36, No. Especial, 2005, 8 Pages, Can be retrieved at <URL:http://revista.cnic.edu.cu/revistaCB/sites/default/files/articulos/CB-2005-4-CB-113.pdf>. With English Abstract.

European Patent Office, European Search Report and Opinion, European Patent Application No. 16852418.9, dated Apr. 8, 2019, eleven pages.

\* cited by examiner

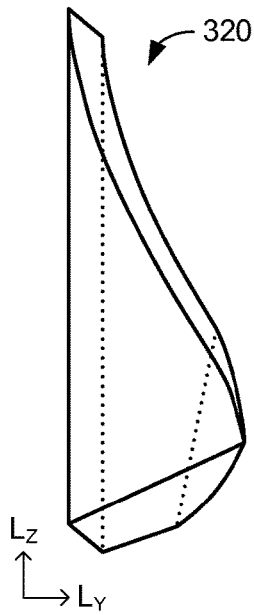
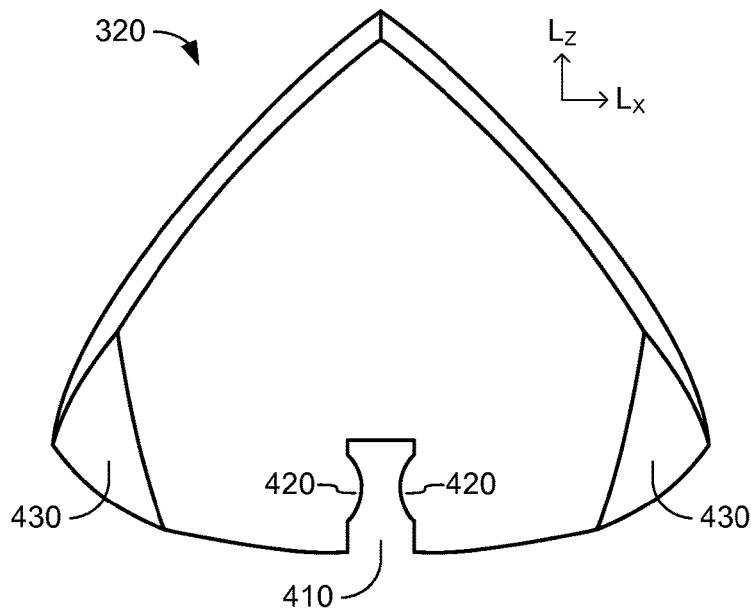
FIG. 4A  FIG. 4B
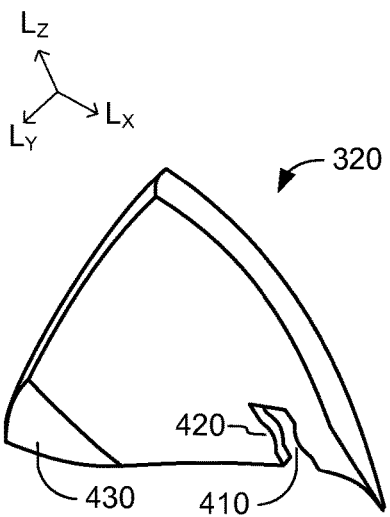
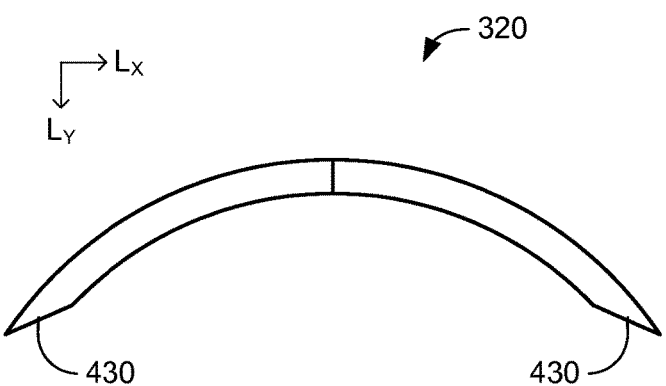
FIG. 4D  FIG. 4C

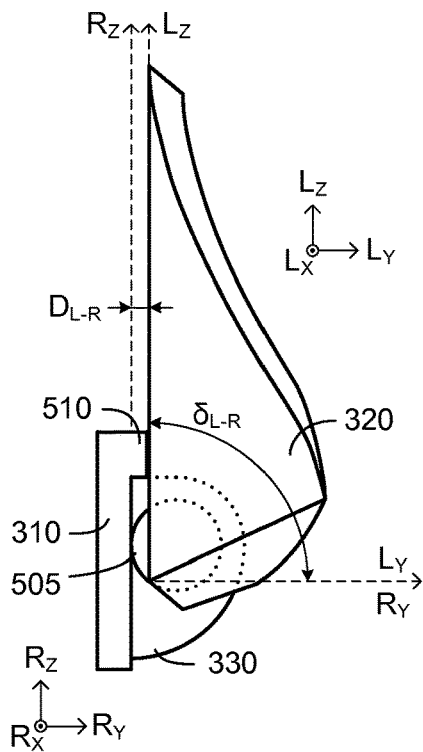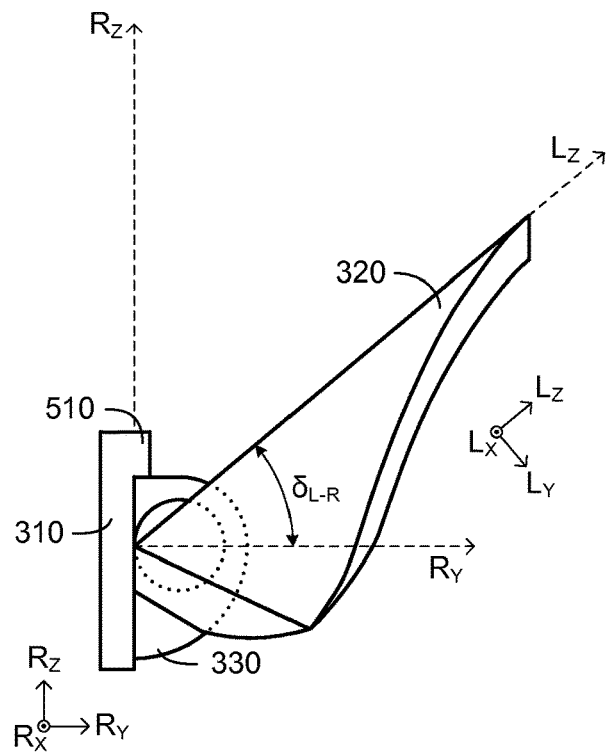
FIG. 5A  FIG. 5B
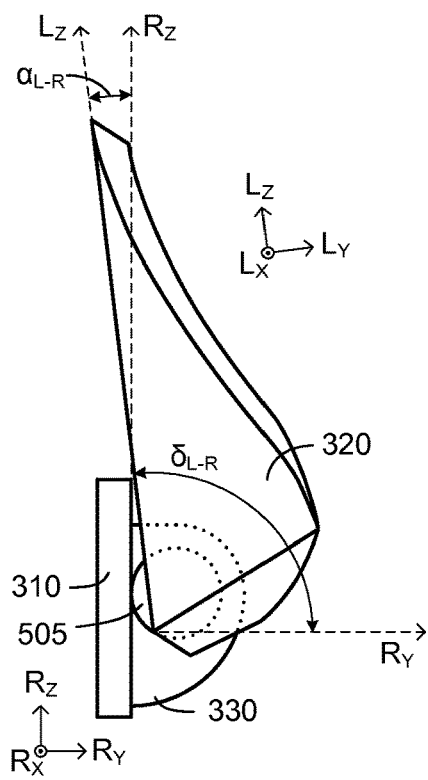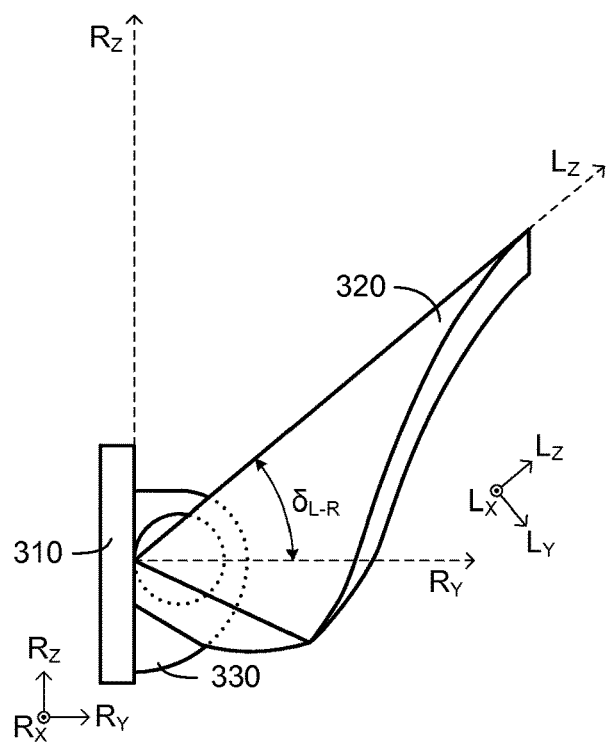
FIG. 6A  FIG. 6B

TRILEAFLET MECHANICAL PROSTHETIC HEART VALVE

BACKGROUND

1. Field of Art

The disclosure generally relates to the field of prosthetic heart valves, and more specifically to trileaflet mechanical prosthetic heart valves.

2. Description of the Related Art

When one of the valves inside a patient's heart does not work properly, the heart valve may be replaced with a prosthetic valve. Heart valve diseases may be classified into two different categories: regurgitation and stenosis. Regurgitation, or backflow, occurs if a valve doesn't close tightly. Blood leaks back into the chambers rather than flowing forward through the heart or into an artery. Stenosis occurs if the flaps of a valve thicken, stiffen, or fuse together. This prevents the heart valve from fully opening. As a result, not enough blood flows through the valve.

Prosthetic heart valves can be categorized into two main categories: mechanical prosthetic heart valves, and tissue or bio-prosthetic heart valves. Mechanical prosthetic heart valves are durable and may last throughout the remainder of the patient's lifetime. Currently existing mechanical prosthetic heart valves do not mimic a human natural heart valve shape. Even in the fully opened position, leaflets may partially block the passage of blood through the valve causing turbulence in the blood. The increased turbulence in the blood increases the probability of coagulation of the blood near the regions of high turbulence around the mechanical prosthetic heart valve. Patients with mechanical prosthetic heart valves oftentimes take anticoagulants and/or blood thinners to prevent blood clots from forming and causing a malfunction of the mechanical prosthetic heart valve and/or turning into an embolism. In addition, the opening and closing of the leaflets causes wear and tear near the interface between the leaflets and the hinges to which the leaflets are attached. The leaflets may also be susceptible to being stuck in the opened position if the leaflets open past a threshold angle which causes the backwards blood flow to push the leaflets on the wrong side, holding the leaflets in the opened position instead of pushing the leaflets to rotate to the closed position.

Tissue valves are made from valves of an animal donor or another animal tissue that is strong and flexible. Tissue valves can last 10 to 20 years and patients with prosthetic tissue heart valves do not need to take anticoagulants or blood thinners. The likelihood of a prosthetic tissue heart valve to malfunction later in the patient's life due to wear and tear is higher than of mechanical prosthetic heart valves, and thus, patients with prosthetic tissue heart valves may additionally have a second heart surgery to replace the prosthetic tissue heart valve.

SUMMARY

Disclosed is a mechanical prosthetic heart valve having a ring, multiple hinges and multiple leaflets. For example the valve can include a ring with three hinges and three leaflets to form a trileaflet mechanical prosthetic heart valve. This trileaflet design mimic's the natural human heart valve shape and functions in a similar way to the natural human valve. The ring of the heart valve can include multiple protrusions located along an inner circumference of the ring that prevent the leaflets from opening beyond a certain point, thus avoiding the possibility of the backwards blood flow being able to hold the leaflets in an open position. For instance, a trileaflet mechanical prosthetic heart valve includes three protrusions located along an inner circumference of the ring. The hinges are attached to the ring and are evenly spaced from one another along the inner circumference of the ring. Each leaflet is attached to one of the hinges by an opening located in the center of the lower portion of the leaflets. The hinges can be positioned in the middle of each leaflet allowing the leaflets to swing open and closed along the hinges, and maximizing freedom of movement of the leaflets since each has its own hinge to rotate around. The position of the hinges and the leaflets relative to the ring is such that the leaflets are immediately adjacent to the ring when open and any blockage of the blood flow through the valve by the leaflets is minimized, as well as minimizing turbulence in the blood flow. The leaflets have a unique shape and curvature such that, when open, they generally mimic the shape of the ring, further limiting their interference with the blood flow.

In some embodiments, the mechanical prosthetic heart valve is covered by a bio-hemo-compatible material. Furthermore, the ring, the hinges, and the leaflets may be composed of titanium, or other materials. In some embodiments, the ring, hinges, and leaflets are composed of titanium coated with a layer of a bio-hemo-compatible material, such as, titanium oxide.

The protrusions of the ring prevent the leaflets from forming an angle that is greater than 90° with respect to the transversal plane of the ring. Since the leaflets cannot open to greater than 90°, it is not possible for the blood to flow against the leaflets on the wrong side of the leaflets such that they are held in an open position and prevented from closing. Instead, the leaflets rotate open as blood flows through the valve and immediately rotate back to the closed position afterwards to prevent backflow. By limiting the opening angle of the leaflets, wear and tear of the hinges and leaflets, as well as the probability of malfunction of the mechanical prosthetic heart valve are reduced. In addition, limiting the opening angle of the leaflets may increase the opening and closing speed of the leaflets, thus improving performance of the mechanical prosthetic heart valve when the patient is experiencing an elevated cardiac frequency. The protrusions of the ring may be evenly spaced relative to each other along the inner circumference of the ring. For instance, the protrusions may be located on an upper portion of the hinges.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

FIG. 4A illustrates a side view of a leaflet of the trileaflet mechanical prosthetic heart valve, according to one embodiment.

FIG. 4B illustrates a front view of the leaflet of the trileaflet mechanical prosthetic heart valve, according to one embodiment.

FIG. 4C illustrates a top view of the leaflet of the trileaflet mechanical prosthetic heart valve, according to one embodiment.

FIG. 4D illustrates a perspective view of the leaflet of the trileaflet mechanical prosthetic heart valve, according to one embodiment.

FIG. 5A illustrates a side view of a portion of a trileaflet mechanical prosthetic heart valve with leaflets in the opened position, according to one embodiment.

FIG. 5B illustrates a side view of a portion of a trileaflet mechanical prosthetic heart valve with leaflets in the closed position, according to one embodiment.

FIG. 6A illustrates a side view of a portion of a trileaflet mechanical prosthetic heart valve without a leaflet stopper and with leaflets in the opened position, according to one embodiment.

FIG. 6B illustrates a side view of a portion of a trileaflet mechanical prosthetic heart valve without a leaflet stopper and with leaflets in the closed position, according to one embodiment.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

The Human Heart

Figure 1:
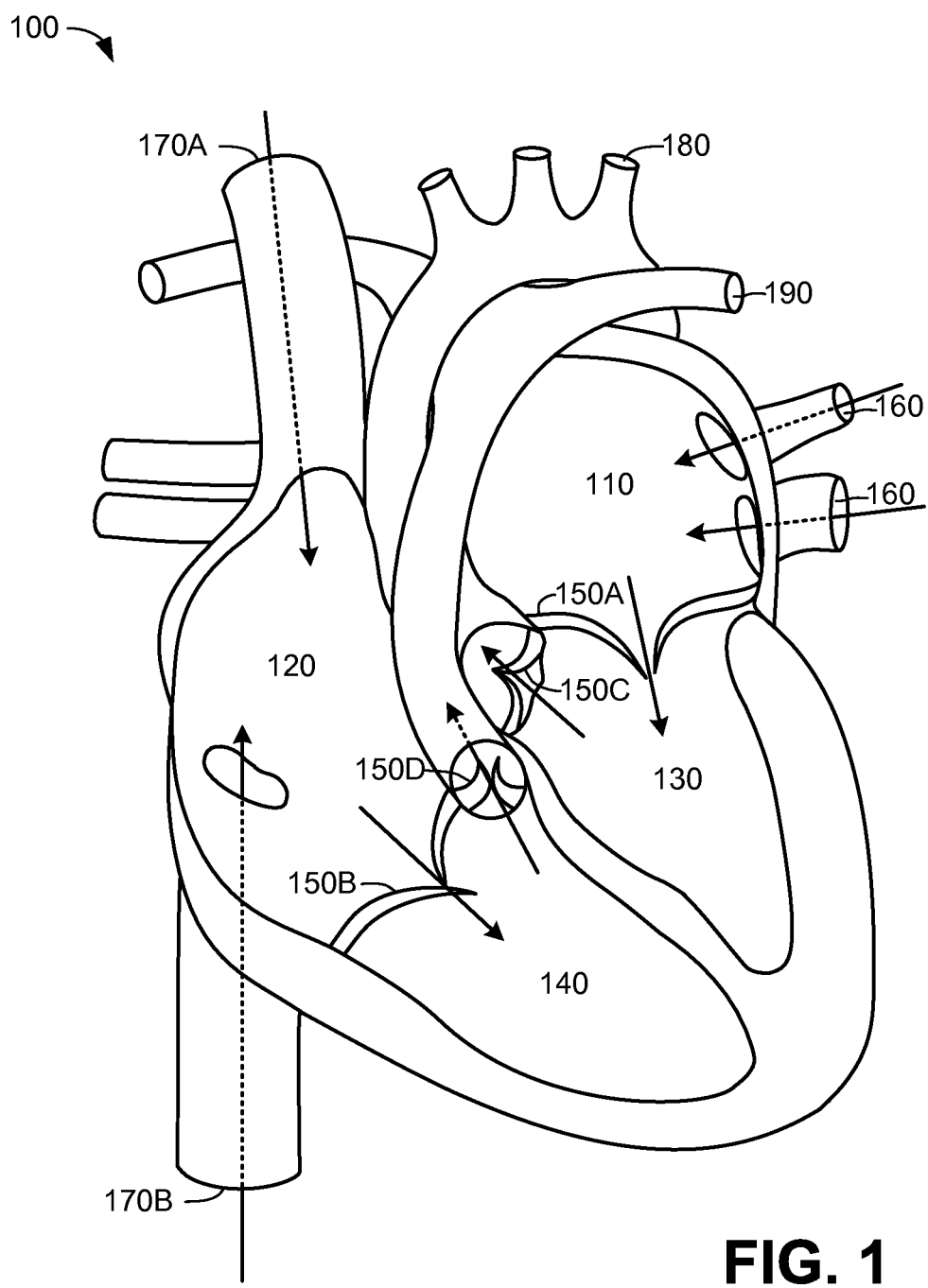
FIG. 1 illustrates a human heart.

FIG. 1 illustrates the human heart. The human heart is divided into four chambers. The left atrium 110, the right atrium, 120, the left ventricle 130, and the right ventricle 140. The heart further includes multiple valves that allow the flow of blood in one direction, and block the flow of blood in the opposite direction.

For instance, during ventricular diastole, blood from the pulmonary veins 160 enters the left atrium 110 and continues flowing through the mitral valve 150A into the left ventricle 130. Similarly, blood from the superior vena cava 170A and the inferior vena cava 170B enters the right atrium 120 and continues flowing through the tricuspid valve 150B into the right ventricle. During the ventricular diastole, the aortic valve 150C prevents blood from the aorta 180 to flow back into the left ventricle 130, and the pulmonary valve 150D prevents blood from the pulmonary artery 190 to flow back into the right ventricle 140.

During ventricular systole, blood from the left ventricle 130 flows out of the heart 100 into the aorta 180 through the aortic valve 150C and blood from the right ventricle 140 flows out of the heart 100 into the pulmonary artery 190 through the pulmonary valve 150D. During ventricular systole, the mitral valve 150A prevents blood from the left ventricle from flowing back into the left atrium 110, and the tricuspid valve 150B prevents blood from the right ventricle from flowing back into the right atrium 120.

During the lifetime of a person, the valves 150 of the heart may deteriorate or become defective. For instance, a heart valve 150 may not be able to fully open due to stiff or fused leaflets (valvular stenosis). In this case, a narrowed opening of the heart valve 150 may cause the heart work harder than a heart with a normal valve to allow blood flow through the defective heart valve. Additionally, a heart valve 150 may be unable to fully close, allowing some of the blood to leak backwards across the valve (valvular insufficiency). In this case, the leak in the heart valve 150 may cause the heart to work harder to compensate for the backward blood flow.

To treat a patient with a deteriorated or defective heart valve, a prosthetic heart valve may be used to replace the deteriorated or defective heart valve.

Figure 2A:
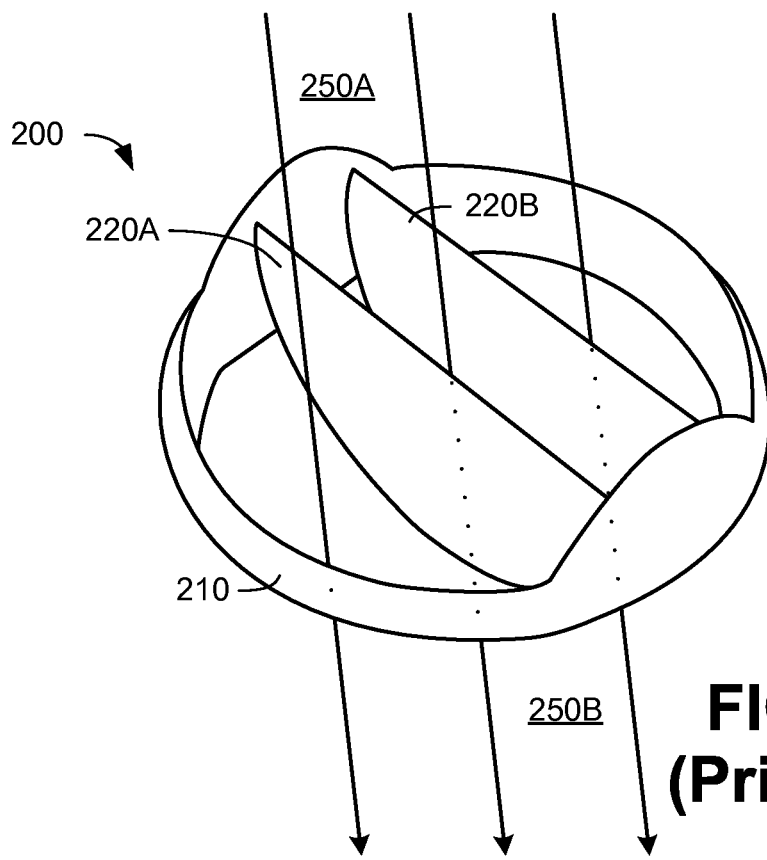
FIG. 2A illustrates a conventional mechanical prosthetic heart valve 200 with leaflets 220 in an opened position.
Figure 2B:
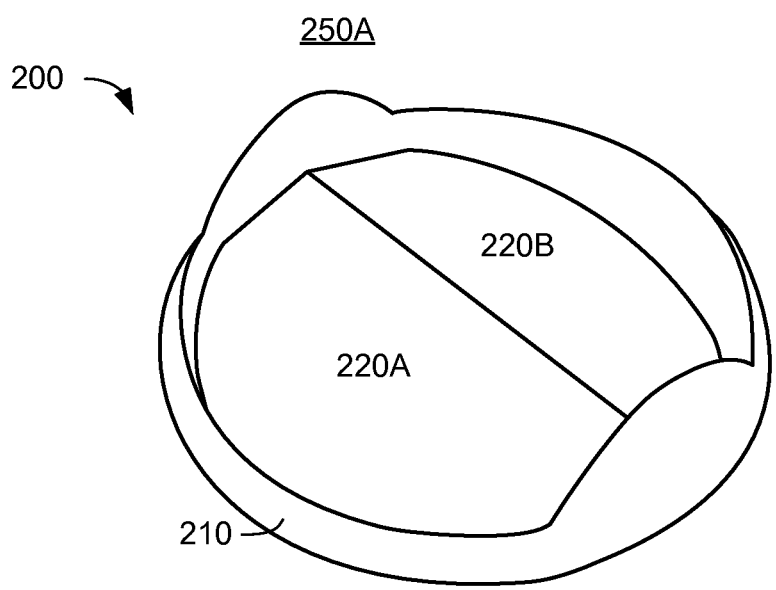
FIG. 2B illustrates a conventional mechanical prosthetic heart valve 200 with leaflets 220 in a closed position.

FIG. 2A illustrates a conventional mechanical prosthetic heart valve 200 with leaflets 220 in an opened position; and FIG. 2B illustrates a conventional mechanical prosthetic heart valve 200 with leaflets 220 in a closed position. The conventional mechanical prosthetic heart valve 200 includes a ring 210 and two leaflets 220. When the leaflets 220 of the prosthetic heart valve 220 are in the opened position, blood may flow from a first side 250A of the heart valve 200 to a second side 250B of the heart valve 200. As illustrated in FIG. 2A, blood may flow through an opening between leaflet 220A and ring 210, an opening between leaflet 220A and leaflet 220B, or an opening between leaflet 220B and ring 210. This increases the amount of turbulence in the blood flow increasing the probability of thrombogenicity and hemolysis. The same is true of any prior design in which a portion of the leaflets sits within the blood flow path, as opposed to being positioned closely to the ring such that a minimal portion of each leaflet is in the blood flow path.

Trileaflet Mechanical Prosthetic Heart Valve

Figure 3A:
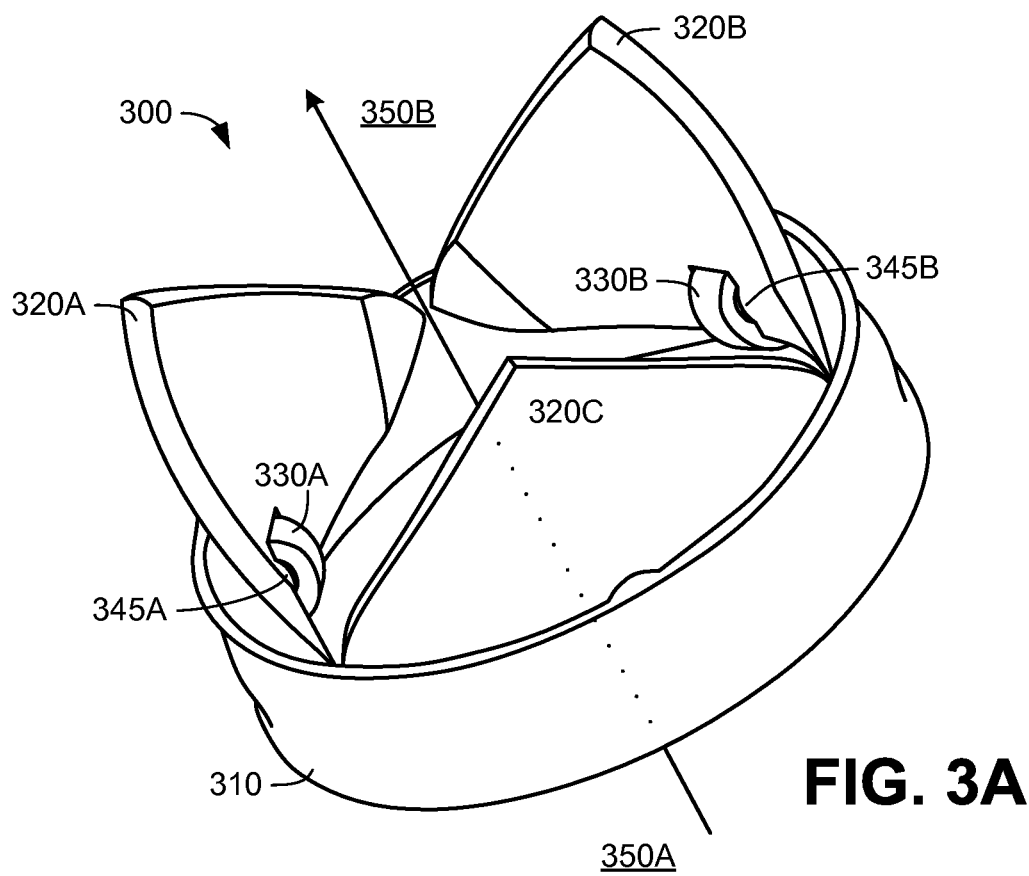
FIG. 3A illustrates a trileaflet mechanical prosthetic heart valve with leaflets in an opened position, according to one embodiment.
Figure 3B:
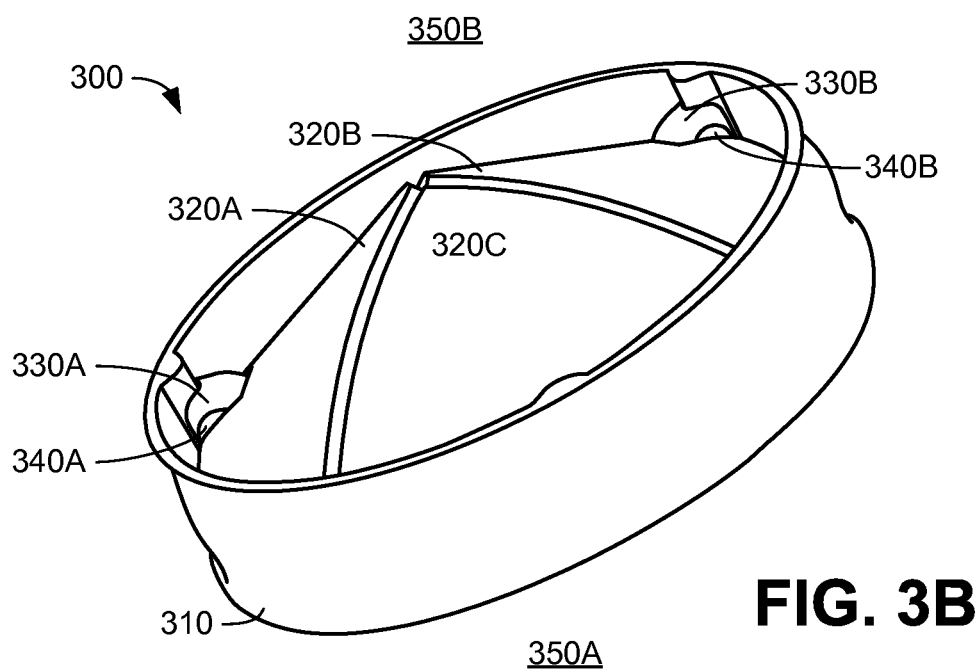
FIG. 3B illustrates the trileaflet mechanical prosthetic heart valve with leaflets in a closed position, according to one embodiment.
Figure 3C:
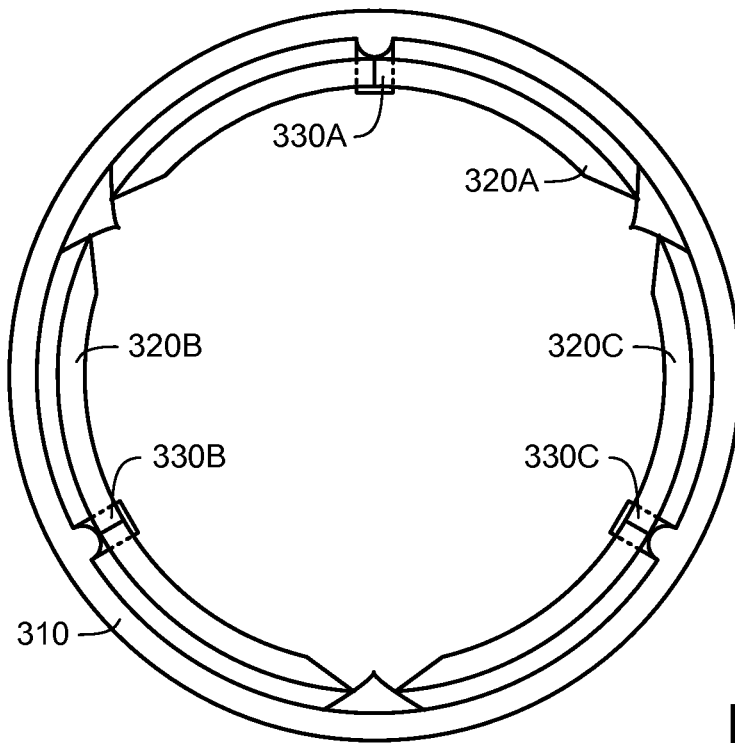
FIG. 3C illustrates a top view of the trileaflet mechanical prosthetic heart valve with leaflets in an opened position, according to one embodiment.
Figure 3D:
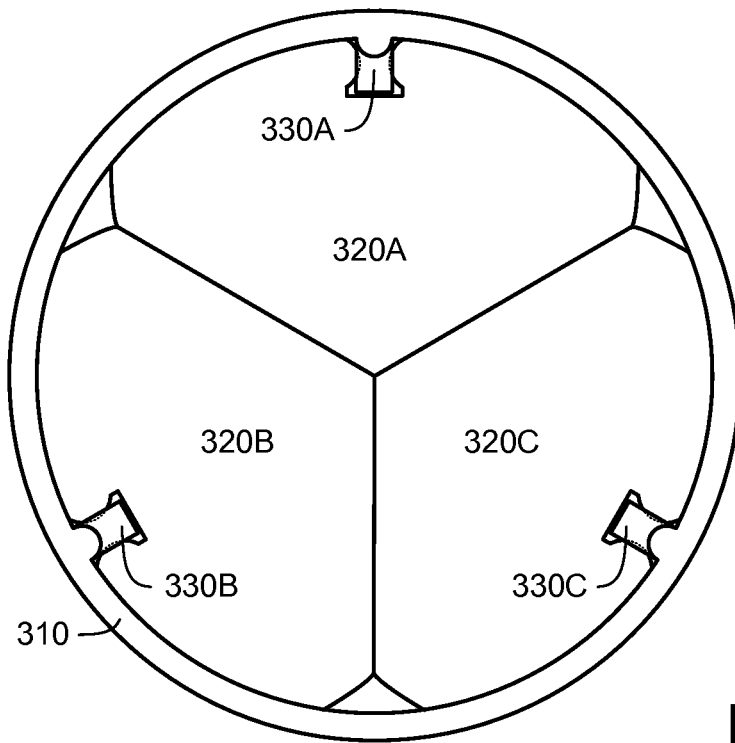
FIG. 3D illustrates a top view of the trileaflet mechanical prosthetic heart valve with leaflets in the closed positions, according to one embodiment.

FIGS. 3A-3D illustrate a trileaflet mechanical prosthetic heart valve, according to some embodiments. FIG. 3A illustrates a trileaflet mechanical prosthetic heart valve 300 with leaflets 320 in an opened position; FIG. 3B illustrates the trileaflet mechanical prosthetic heart valve 300 with leaflets 320 in a closed position; FIG. 3C illustrates a top view of the trileaflet mechanical prosthetic heart valve 300 with leaflets 300 in the opened position; and FIG. 3D illustrates a top view of the trileaflet mechanical prosthetic heart valve 300 with leaflets 320 in the closed position, according to one embodiment.

The trileaflet mechanical heart valve 300 includes a ring 310, three leaflets 320 (320A, 320B, 320C), and three hinges 330 (330A, 330B, 330C). In some embodiments, a mechanical prosthetic heart valve may include additional leaflets and hinges. The hinges 330 rotably attach the leaflets 320 to the ring 310. The hinges 330 are configured such that each leaflet 320 opens and closes by sliding along the hinges at an opening located at the central lower portion of the leaflet 320. Each hinge 330 may include an open area 340 in the middle of the hinge where protuberances 345 located at the sides of the opening of the central lower portion of the leaflets attach to the hinge 330. In some embodiments, the leaflets 320 are slidable along the hinge. The leaflets 320 are configured to open as shown in FIG. 3A and FIG. 3C to allow the flow of blood from a first side 350A of the heart valve to a second side 350B of the heart valve. Furthermore, the leaflets 320 are configured to close as shown in FIG. 3B and FIG. 3D to block the backward blood flow from the second side 350B of the heart valve to the first side 350A of the heart valve.

FIG. 4A illustrates a side view of a leaflet 320 of the trileaflet mechanical prosthetic heart valve 300; FIG. 4B illustrates a front view of the leaflet 320 of the trileaflet mechanical prosthetic heart valve 300; FIG. 4C illustrates a top view of the leaflet of the trileaflet mechanical prosthetic heart valve; and FIG. 4D illustrates a perspective view of the leaflet of the trileaflet mechanical prosthetic heart valve, according to one embodiment. Leaflet 320 has a generally triangular shape. Furthermore, leaflet 320 is flat in the longitudinal axis and concave-convex in the transversal axis. In some embodiments, the leaflets are cut from a cylindrical piece. As such, as shown in FIGS. 3A and 3C, when the leaflets 320 are in the opened position, the outer contour of the leaflets 320 substantially tracks the inner contour of the ring 310 of the heart valve 300. Thus, this increases the effective opening area of the heart valve 300, and allows for a better laminar flow and reduction of the turbulence of the blood passing through the heart valve 300. In some embodiments, the distance between each leaflet and the ring when the leaflets are open ($D_{L-R}$) is no more than 1 mm at any point around the circumference of the ring.

The improved laminar flow of heart valve 300 reduces the probability of thrombogenicity and hemolysis thus, reducing the need of a patient using the prosthetic mechanical heart valve 300 of taking anticoagulants.

The bottom portion of the leaflet 320 has a curved shape that substantially tracks the inner contour of the ring 310 of the heart valve 300 when the leaflets are in the closed position. Additionally, the bottom portion of the leaflet 320 includes an opening 410 for coupling the leaflet 320 to the hinge 330. The leaflet 320 additionally includes at least two protuberances 420 along the sides of the opening 410 guide the movement of the leaflets. In one embodiment, the protuberances 420 form a first portion of the opening 410 above the protuberance and a second portion of the opening 410 between the protuberances. The first portion of the opening 410 is wider than the second portion of the opening 410. In some embodiments, the opening 410 includes a third portion below the protuberances 420 that is wider than the second portion of the opening 410. The third portion of the opening 410 may be configured to engage and slide over the hinge during the opening of the leaflet 320.

The leaflet 320 is coupled to the ring 310 from a single point located at the center of the transversal axis of the leaflet 320. This prevents the leaflet from separating from the ring 310 during the opening of the leaflet increasing the size of the central opening of the heart valve 300 and reducing the amount of blood that passes thought the valve from the opening between the leaflet 320 and the ring 310. As such, turbulence of the blood passing through the heart valve 300 is reduced, thus reducing the probability of thrombogenicity and hemolysis.

For fluid dynamics reasons, leaflets 320 further include a flat region 430. Flat regions 430 are located on the left end and the right end of the leaflet 320.

Figure 4E:
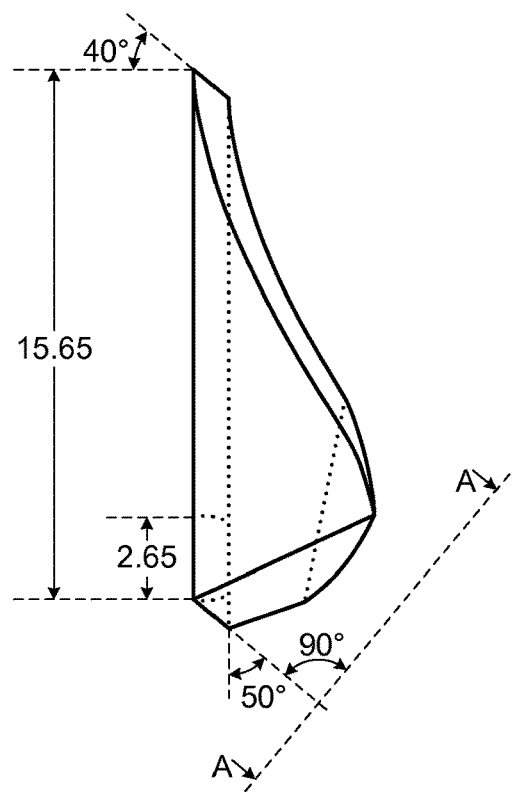
FIG. 4E illustrates a side view of a leaflet 320 of the trileaflet mechanical prosthetic heart valve 300 showing the dimensions of the leaflet 320, according to one embodiment.
Figure 4F:
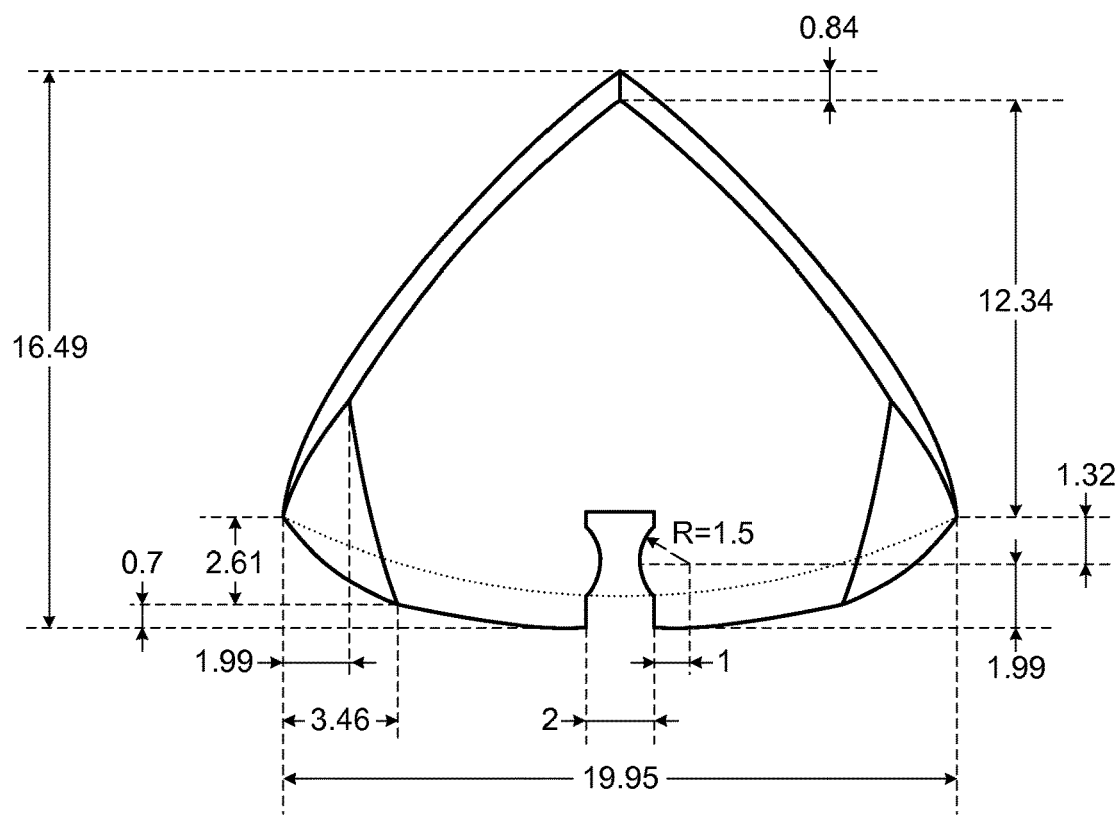
FIG. 4F illustrates a front view of the leaflet 320 of the trileaflet mechanical prosthetic heart valve 300 showing the dimensions of the leaflet 320, according to one embodiment.
Figure 4G:
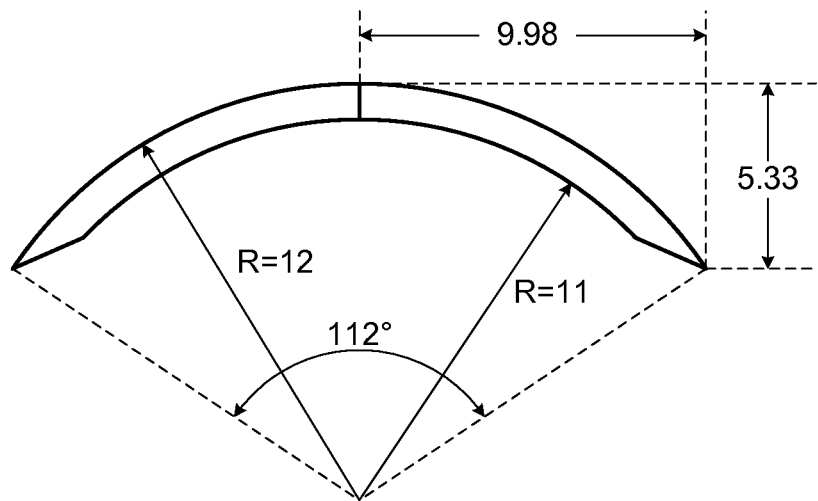
FIG. 4G illustrates a top view of the leaflet 320 of the trileaflet mechanical prosthetic heart valve 300 showing the dimensions of the leaflet 320, according to one embodiment.
Figure 4H:
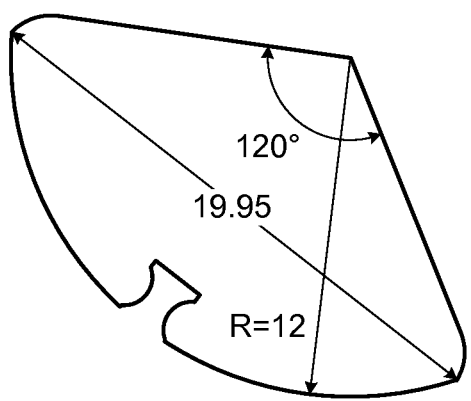
FIG. 4H illustrates an auxiliary view of the leaflet 320 of the trileaflet mechanical prosthetic heart valve 300 showing the dimensions of the leaflet 320, according to one embodiment.
Figure 7:
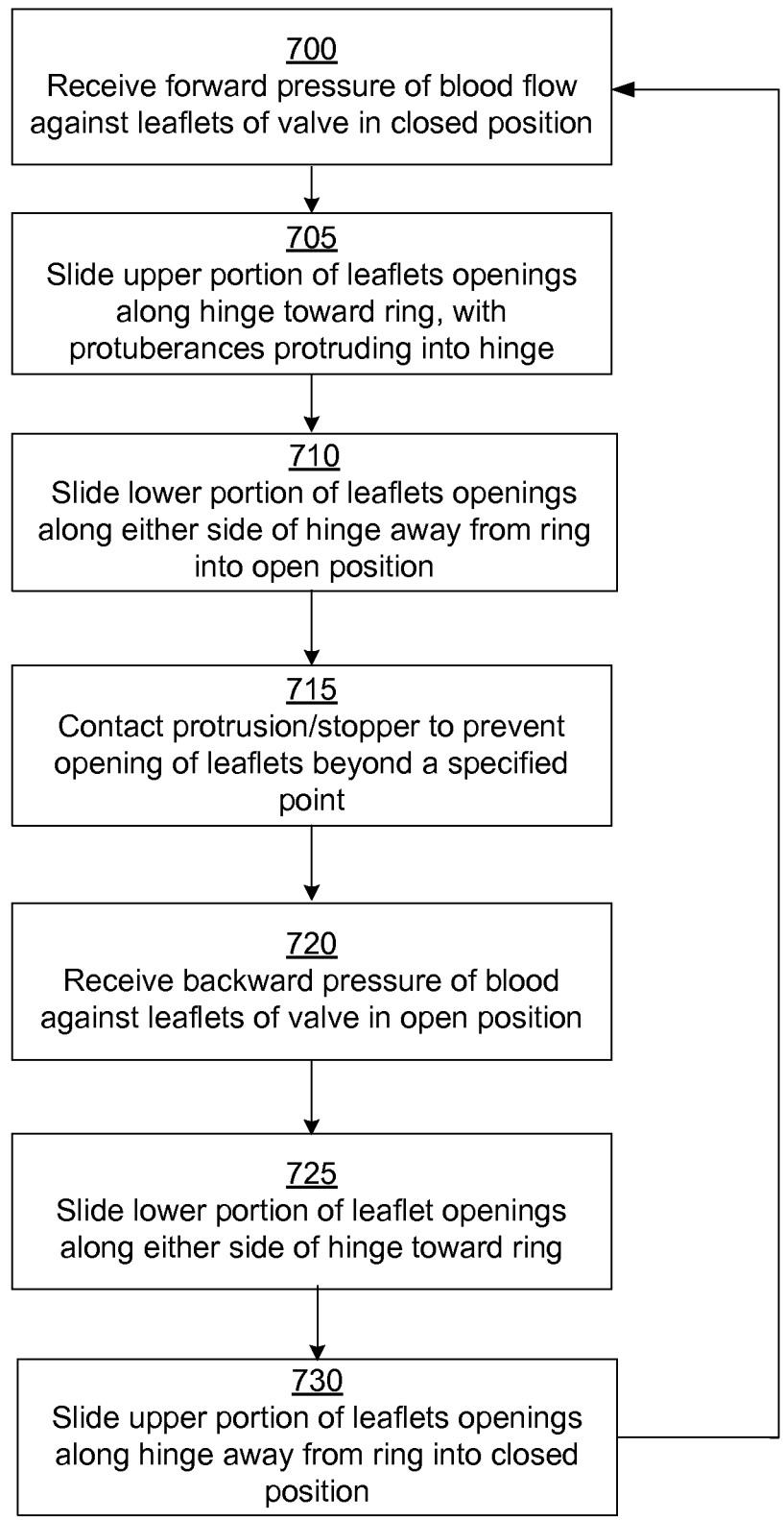
FIG. 7 is a flow chart illustrating a method of operation of a trileaflet mechanical prosthetic heart valve, according to one embodiment.

FIG. 4E illustrates a side view of a leaflet 320 of the trileaflet mechanical prosthetic heart valve 300 showing the dimensions of the leaflet 320; FIG. 4F illustrates a front view of the leaflet 320 showing the dimensions of the leaflet 320; FIG. 4G illustrates a top view of the leaflet 320 showing the dimensions of the leaflet 320; and FIG. 4H illustrates an auxiliary view of the leaflet 320 across the AA plane shown in FIG. 4E showing the dimensions of the leaflet 320, according to one embodiment. The leaflet 320 has a height of 16.49 mm and a width of 19.95 mm. The leaflet 320 has a closing angle of 35°. Opening 410 has a width of 2 mm, and protuberances 420 have a radius of 1.5 mm. The leaflets further have an outer radius of 12 mm and an inner radius of 11 mm.

The size of the leaflet shown in FIG. 4E-4H is exemplary for replacing the aortic valve of an adult with an average size heart, and may be scaled up or down depending on the many factors including the size of the heart of the patient, and the heart valve being replaced by the trileaflet mechanical prosthetic heart valve 300. For instance, the leaflets used for a mitral valve of an adult with an average size heart may be scaled up or down compared to the leaflets shown in FIG. 4E-4H.

FIG. 5A illustrates a side view of a portion of the trileaflet mechanical prosthetic heart valve 300 with a leaflet 320 in the opened position; and FIG. 5B illustrates a side of the trileaflet mechanical prosthetic heart valve 300 with the leaflet 320 in the closed position. As illustrated in FIG. 5A, when the leaflets are in the opened position, the leaflets form an angle substantially perpendicular to the transverse plane ($R_Y$-$R_X$ plane) of the ring 310. As illustrated in FIG. 5B, when the leaflets are in the closed position, the longitudinal plane of the leaflets 320 form an angle larger than 0° with the transverse plane of the ring 310. In some embodiments, the longitudinal plane ($L_Z$-$L_X$ plane) of the leaflets 320 may form an angle ($\delta_{L-R}$) larger 35° with the transverse plane of the ring 310. This reduces the swing or trajectory of the leaflets from the closed position to the opened position and vice versa, reducing the amount of time for the heart valve 300 to open and close. As such, the trileaflet mechanical prosthetic heart valve 300 may function properly even when the patient is experiencing an elevated cardiac frequency.

In one embodiment, the ring 310 includes stoppers 510 that prevent the leaflets 320 from opening beyond a certain angle. For instance, stoppers 510 prevent the leaflets 320 from opening beyond 90° with respect to the transversal plane of the ring 310 (i.e., stoppers 510 prevent $\delta_{L-R}$ from exceeding 90°). Preventing the leaflets 320 from opening beyond 90° with respect to the transversal plane of the ring 310 reduces the turbulence of the blood caused by the leaflets 320, and reduces the swing or trajectory of the leaflets 320 during the closing and opening of the heart valve 320 (thus reducing the closing and opening time of the heart valve 300, and the wear and tear of the leaflets 320), and reduces the probability of a leaflet from being stuck in the opened position. For example, backflow of blood in the wrong direction in the valve could potentially create a force against the leaflet to hold the leaflet in the open position if the leaflet is allowed to open beyond 90° with respect to the transversal plane of the ring 310. FIGS. 5A and 5B show one example of the stoppers 510. The stoppers can be otherwise positioned on the ring or shaped differently. For example, the stoppers can be positioned directly above the hinge at the top of the ring or in the middle of the ring. As another example, there can be a stopper positioned on the hinge to stop the lower portion of the leaflet from moving away from the ring beyond a point that positions the ring at 90° with respect to the transversal plane of the ring.

FIGS. 5A and 5B also illustrate an open area 505 of the hinge 330. The hinge attaches at either end around to the ring to form the open area 505. The open area 505 is shown as circular in the figures, but it can be otherwise shaped. The protuberances 420 (shown in FIG. 4B) of the leaflets protrude into this open area 505 of the hinge 330, as is generally visible in FIGS. 3A and 3B. These protuberances ensure the leaflets remain attached to the valve even though the leaflets are open below the protuberances, as shown in FIG. 4B. The wider portion (or first portion) of the opening 410 of the leaflet (above the narrower portion or second portion into which the protuberances protrude, as shown in FIG. 4B), engages the hinge and allows the leaflet to slide freely along the hinge to rotate open or closed. The lower wider portion (or third portion) below the protuberances is open to the base of the leaflet. This lower wide portion that is open to the leaflet base allows the leaflet to open by sliding over an engaging the hinge. When the leaflet is closed, this lower portion is generally aligned with the open area 505 of the hinge, but as the leaflet opens, this lower portion slides over one end of the hinge on either side of the hinge, allowing the leaflet to open freely.

FIG. 6A illustrates a side view of a portion of a trileaflet mechanical prosthetic heart valve without a leaflet stopper, with leaflets in the opened position; and FIG. 6B illustrates a side view of the portion of the trileaflet mechanical prosthetic heart valve without a leaflet stopper, with leaflets in the closed position, according to one embodiment. The leaflets 320 of the heart valve without stoppers 510, when closed, are positioned similarly to the leaflets 320 of the heart valve with stoppers 510. Conversely, when the leaflets 320 are in the opened position, the leaflets 320 may be positioned at an angle larger than 90° with respect to the transversal plane of the ring 310.

Since each leaflet 320 is independently attached to the ring through an independent hinge 330, each leaflet may open and close independently of the other leaflets. Thus, if the movement of a leaflet is partially or completely limited (i.e., a leaflet may not completely open or close), the other two leaflets may continue functioning properly, reducing the probability of an acute deterioration of the patients health.

In some embodiments, the ring 310, leaflets 320, and hinges 330 are composed of a metallic material. For instance, the ring 310, leaflets 320, and hinges 330 may be composed of titanium or a combination of titanium with titanium oxide or a combination of titanium with other materials. Further, the trileaflet mechanical prosthetic heart valve 300 may be covered with a bio-hemo-compatible material (e.g., titanium oxide).

Moreover, the trileaflet mechanical prosthetic heart valve 300 may be used as a prosthetic implant for replacement of any of the four natural heart valves in humans, in case of dysfunction, congenital defects, or acquired complications. The replacement of a human heart valve with the trileaflet mechanical prosthetic heart valve 300 may be performed by a surgical procedure at open heart. Furthermore, the trileaflet mechanical prosthetic heart valve 300 may be used in blood pumps, devices for partial circulatory support, in heart prosthesis completely implantable or of external use, and can also be used in vascular conducts made of biological or synthetic material used surgery of large conducts, such as the ascendant aorta and pulmonary trunk.

Method of Operation of Trileaflet Mechanical Prosthetic Heart Valve

In use, the heart valve, such as the trileaflet mechanical prosthetic heart valve described above, operates similarly to a natural human heart valve. Initially, the leaflets of the valve can sit in a closed position, as shown in FIGS. 3B and 3D. The leaflets, when closed, may be positioned at approximately 35° with respect to the transversal plane of the ring, as shown in FIG. 3B. As the heart muscles contract, blood is advanced within the heart from one chamber to another or between chambers and blood vessels in the direction shown in FIG. 3A. The muscle contraction causes the blood to put pressure on the valve in the direction shown in FIG. 3A to push the leaflets open. As the valve receives 700 pressure due to the blood flow, the leaflets each swing along their individual hinges into an open position. Specifically, the opening of the leaflets allows the upper portion of the leaflet opening to slide 705 along the hinge toward the ring, with the upper wider portion of the opening generally surrounding the arm of the hinge and with the protuberances protruding into the open area of the hinge. The protuberances ensure that the leaflet does not disengage from the hinge during opening and closing. As the leaflet continues to open, the lower wider portion of the leaflet opening slides 705 over the hinge on either side of the hinge to allow the base of the leaflet move along the hinge, moving the lower portion of the opening away from the ring.

Where the valve includes protrusions or another stopping mechanism, the leaflets swing open until they contact 710 the protrusions/stopping mechanism, which prevents the leaflets from opening beyond a specified point. For example, the leaflets may be prevented from opening more than 90° with respect to the transversal plane of the ring. In one embodiment, the leaflets, when closed, are positioned at approximately 90° with respect to the transversal plane of the ring, as shown in FIGS. 3A and 3C.

The curvature of the leaflets closely matches the curvature of the ring, as shown in FIG. 3C, so valve has a very low profile when the leaflets are open, minimizing blood flow blockage and turbulence. The leaflets will stay in the open position as the blood flows through from chamber to chamber or between vessel and chamber. Once the blood has passed through the valve, the blood puts reverse pressure on the leaflets in the opposite direction of that shown in FIG. 3A. This receiving 715 of backward pressure causes the leaflets to swing closed. The leaflets each rotate long their individual hinge to slide into a closed position, returning to the position of FIGS. 3B and 3D. Specifically, the lower portion of the opening of the leaflet slides 720 on either side of the hinge closer to the ring and the upper portion of the opening slides 720 along the hinge away from the ring. The leaflets will remain closed until the next contraction of the heart muscles causes blood to again flow through the valve.

Additional Configuration Considerations

Throughout this specification, plural instances may implement components, operations, or structures described as a single instance. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for trileaflet mechanical prosthetic heart valve through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A trileaflet mechanical prosthetic heart valve comprising:
   a ring including three or more protrusions located along an inner circumference of the ring;
   three or more hinges attached to the ring, the three or more hinges evenly spaced from one another along the inner circumference of the ring; and
   three or more leaflets, each leaflet attached to one of the three or more hinges, each leaflet attached to a hinge by an opening located in a center of a lower portion of the leaflet, each leaflet including:
      a front surface having a concave shape in a transverse axis and a flat shape in a longitudinal axis,
      a rear surface having a convex shape in the transverse axis and a flat shape in the longitudinal axis, the rear surface of the leaflets configured to be in contact with the protrusions of the ring when the leaflets are in an open position such that there is an arc shaped gap formed between the rear surface of the leaflets and the inner circumference of the ring when the leaflets are in the open position, wherein the the rear surface of the leaflets substantially tracks the inner circumference of the ring when the leaflets are in the open position; and
      flat regions on left and right sides of the front surface of the leaflets, the flat regions for improved fluid dynamics.

2. The trileaflet mechanical prosthetic heart valve of claim 1, further comprising a bio-hemo-compatible layer of titanium oxide covering the ring, the three or more hinges, and the three or more leaflets.

3. The trileaflet mechanical prosthetic heart valve of claim 1, wherein the ring, the three or more hinges, and the three or more leaflets are composed of titanium.

4. The trileaflet mechanical prosthetic heart valve of claim 1, wherein the leaflets have a concave-convex cross section along a transversal plane of the leaflets.

5. The trileaflet mechanical prosthetic heart valve of claim 1, wherein the leaflets each have a generally triangular shape.

6. The trileaflet mechanical prosthetic heart valve of claim 1, wherein the lower portion of the leaflets together form a circular shape along the inner circumference of the ring.

7. The trileaflet mechanical prosthetic heart valve of claim 1, wherein the protrusions of the ring are configured to prevent the leaflets from forming an angle greater than 90° with respect to a transversal plane of the ring.

8. The trileaflet mechanical prosthetic heart valve of claim 1, wherein the protrusions are evenly spaced relative to each other along the inner circumference of the ring.

9. The trileaflet mechanical prosthetic heart valve of claim 1, wherein the hinges are coupled to the ring at a lower portion of the protrusions.

10. The trileaflet mechanical prosthetic heart valve of claim 1, wherein the protrusions of the ring have a semi-circular cross section.

11. The trileaflet mechanical prosthetic heart valve of claim 1, wherein the hinges are configured such that each leaflet opens and closes by sliding along the hinge at the opening in the center of the lower portion of the leaflet.

12. The trileaflet mechanical prosthetic heart valve of claim 1, wherein the leaflets are configured to be positioned at 35° with respect to a transversal plane of the ring when closed and at 90° with respect to the transversal plane of the ring when open.

13. The trileaflet mechanical prosthetic heart valve of claim 1, wherein each hinge attaches to the ring at each end of the hinge, the hinge including an open area in a middle of the hinge, and wherein each leaflet is positioned on each hinge such that the hinge sits within the opening of the leaflet.

14. The trileaflet mechanical prosthetic heart valve of claim 13, wherein each leaflet includes protuberances on either side of the opening, the protuberances protruding into the opening.

15. The trileaflet mechanical prosthetic heart valve of claim 14, wherein the protuberances of each leaflet form a first portion of the opening above the protuberance, the first portion being wider than a second portion of the opening between the protuberances, the leaflet being slidable along the hinge with the hinge positioned within the first portion of the opening.

16. The trileaflet mechanical prosthetic heart valve of claim 15, wherein the second portion of the opening of each leaflet is narrowed by the protuberances, the leaflet being slidable along the hinge with the protuberances protruding into the open area of the hinge during opening and closing of the leaflets.

17. The trileaflet mechanical prosthetic heart valve of claim 15, wherein the opening of each leaflet includes a third portion below the protuberances that is wider than the second portion, the third portion being open to a base of the hinge, the third portion configured to engage and slide over the hinge during opening of the leaflet.

18. The trileaflet mechanical prosthetic heart valve of claim 1, each leaflet further comprising:
a bottom surface having a convex shape,
wherein:
the concave shape of the front surface has a first radius of curvature,
the convex shape of the rear surface has a second radius of curvature larger than the first radius of curvature, and
the convex shape of the bottom surface has a third radius of curvature, the third radius of curvature substantially equal to the second radius of curvature.

19. The trileaflet mechanical prosthetic heart valve of claim 1, wherein a distance from the inner circumference of the ring to the rear surface of a leaflet of the three or more leaflets is less than 1 mm at any point around the inner circumference of the ring when the leaflets are in the open position.

20. A trileaflet mechanical prosthetic heart valve comprising:
a ring having an inner circumference and three or more protrusions located along the inner circumference of the ring;
three or more hinges attached to the ring, the three or more hinges evenly spaced from one another along the inner circumference of the ring; and
three or more leaflets, each leaflet cut from a cylindrical piece, each leaflet attached to one of the three or more hinges, each leaflet including flat regions on left and right sides, the flat regions for improved fluid dynamics, each leaflet attached to a hinge by an opening located in a center of a lower portion of the leaflet, each leaflet including protuberances on either side of the opening that protrude into the hinge allowing rotation of the leaflet along the hinge, wherein the leaflets are configured to be in contact with the protrusions of the ring when the leaflets are in an open position, and wherein the leaflets are configured not to be in contact with the protrusions of the ring when the leaflets are in a closed position.

21. The trileaflet mechanical prosthetic heart valve of claim 20, further comprising three or more protrusions located along an inner circumference of the ring, the protrusions of the ring configured to prevent the leaflets from forming an angle greater than 90° with respect to a transversal plane of the ring.

22. The trileaflet mechanical prosthetic heart valve of claim 20, wherein each hinge includes an open area in a middle of the hinge, and wherein each leaflet is positioned on each hinge such that the protuberances protrude into the open area of the hinge to allow the leaflet to be slidable along the hinge for opening and closing of the leaflets.

* * * * *

UNITED STATES PATENT AND TRADEMARK OFFICE
CERTIFICATE OF CORRECTION

PATENT NO. : 10,478,288 B2
APPLICATION NO. : 14/870049
DATED : November 19, 2019
INVENTOR(S) : Osvaldo N. Amerio and Carlos Enrique Schvezov It is certified that error appears in the above-identified patent and that said Letters Patent is hereby corrected as shown below:

On the Title Page

Page 2, Column 1, Item (56) Other Publications, Line 1, Delete ""Disetio" and insert --"Diseño-- therefor In the Claims Column 10, Line 3, In Claim 1, delete "the the" and insert --the-- therefor Signed and Sealed this
Twenty-seventh Day of October, 2020

Andrei Iancu
*Director of the United States Patent and Trademark Office*